United States Patent [19]

Raphael

[11] Patent Number: 5,546,009
[45] Date of Patent: Aug. 13, 1996

[54] DETECTOR SYSTEM USING EXTREMELY LOW POWER TO SENSE THE PRESENCE OR ABSENCE OF AN INERT OR HAZARDOUS FUILD

[76] Inventor: Ian P. Raphael, 112 Ross Creek Ct., Los Gatos, Calif. 95032

[21] Appl. No.: 321,800

[22] Filed: Oct. 12, 1994

[51] Int. Cl.$^6$ .......................... G01R 27/08; G08B 21/00
[52] U.S. Cl. ........................ 324/694; 324/556; 324/696; 324/713; 340/605; 73/40
[58] Field of Search .................... 324/555, 556, 324/693, 694, 696, 705, 713, 722; 73/40, 40.5 R, 46, 49.1, 49.2 T; 340/604, 605, 619, 620

[56] References Cited

U.S. PATENT DOCUMENTS

| | | | |
|---|---|---|---|
| 3,412,325 | 11/1968 | Soderling | 324/693 |
| 3,936,735 | 2/1976 | deBough | 324/694 X |
| 4,122,389 | 10/1978 | Haagen | 324/694 |
| 4,126,857 | 11/1978 | Lancia et al. | 340/605 X |
| 4,845,472 | 7/1989 | Gordon et al. | 340/605 |
| 5,188,143 | 2/1993 | Krebs | 340/605 X |
| 5,240,022 | 8/1993 | Franklin | 340/605 X |
| 5,315,291 | 5/1994 | Furr | 340/605 |

*Primary Examiner*—Kenneth A. Wieder
*Assistant Examiner*—Diep Do
*Attorney, Agent, or Firm*—Claude A. S. Hamrick

[57] ABSTRACT

A fluid detection system capable of detecting the smallest amount of liquid chemicals, mixtures, aqueous solutions, pure water and others by detecting very low levels of resistance or conductance due to ionization when the liquid substances are subjected to very small amounts of electrical power in a small and localized sampling area. The system includes an electronic control module and a sensing probe. The control module provides strictly limited and controlled amounts of electrical voltage and current to one or more remotely located sensing probes which detect the level of resistance or conductance between two electrodes (gold pins) disposed at a fixed distance from one another. The voltage developed across the electrodes is input to a comparator circuit in the electronic module and compared to a reference to produce a signal defining either a dry or a wet (leak) condition of the sensing probe. This signal can be utilized to generate shutdown signals and/or audible and visual alarms. The detection system can also be used to very accurately detect fluid levels.

26 Claims, 5 Drawing Sheets

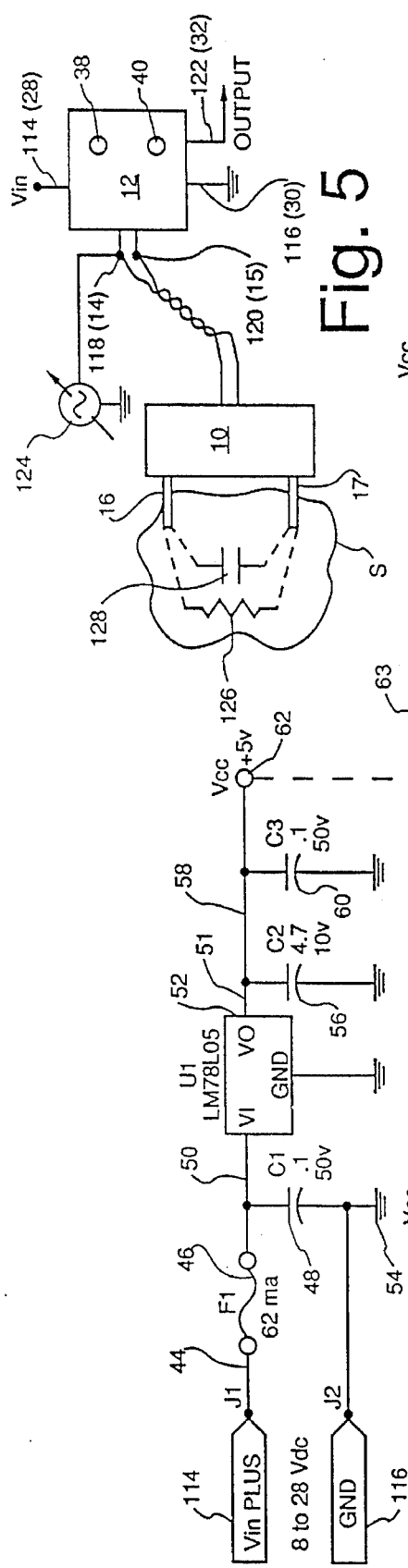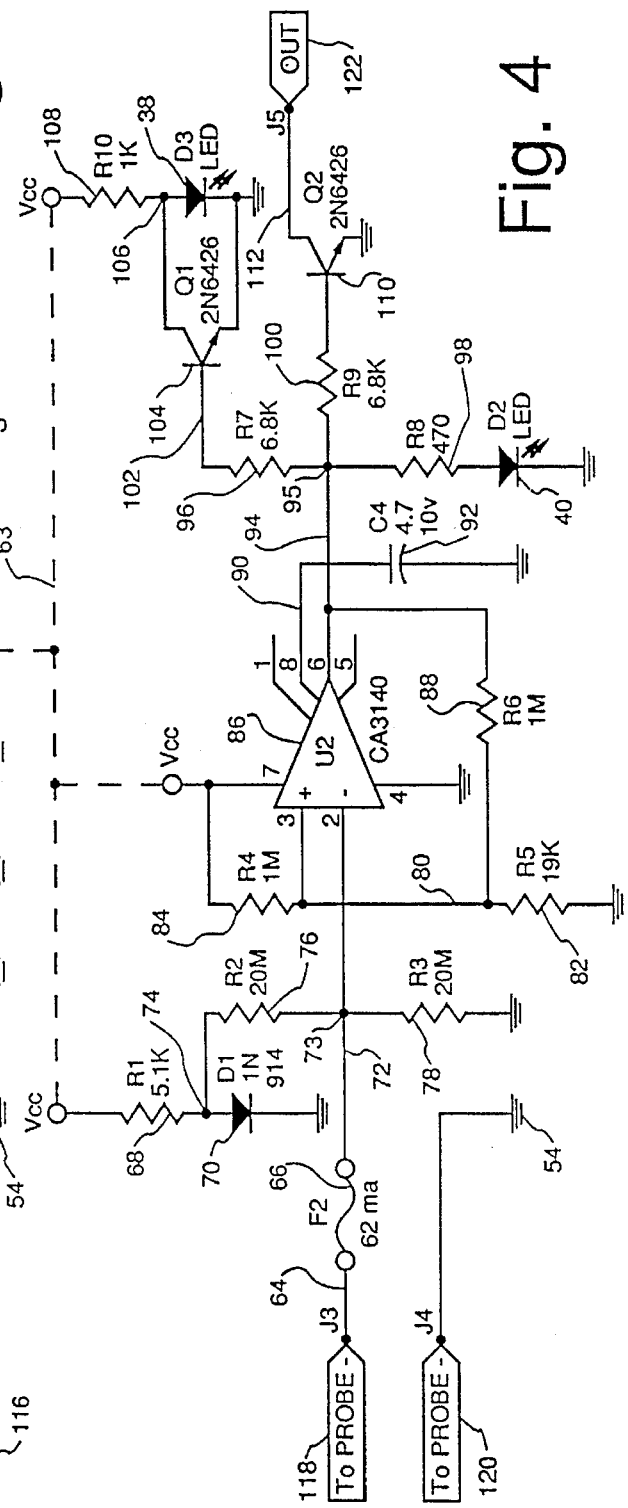

DETECTOR SYSTEM USING EXTREMELY LOW POWER TO SENSE THE PRESENCE OR ABSENCE OF AN INERT OR HAZARDOUS FUILD

BACKGROUND OF THE INVENTION

1. Field of the Invention

The present invention relates generally to the very low-power detection of the resistive or the resistive-capacitive characteristics of certain substances, such as fluids which are either liquid or vaporous, and more particularly to leak or spill detection apparatus for sensing the resistance, or the parallel capacitance and resistance, of a substance as an indication that a leak or spill of the substance has occurred, with one or more remote probes being connected to a single display and alarm unit.

2. Brief Description of the Prior Art

Inert materials, such as air or deionized water, have an extremely high resistance, but are not hazardous or corrosive and in use occasionally require detection by apparatus of the type toward which the present invention is directed. However, hazardous or corrosive fluids, which contain large amounts of ionized material that can combine corrosively or in a hazardous way with other matter in their environment often require detection. Such materials have a relatively low resistance because of ionic conduction and are difficult to monitor or detect.

There are many applications in which it is important that a leak of a hazardous or corrosive fluid be detected as soon as possible after it has occurred. Some of these applications involve corrosive and/or combustible fluids that will explode in the event a spark is generated. Others involve electrolytic but non-explosive fluids that can be detected by simply detecting the ionization process across a pair of electrodes.

In one embodiment of the prior art, a leak detection apparatus is shown in U.S. Pat. No. 5,190,069 for monitoring leakage from household water systems. Upon detection of a leak, the water supply valve is automatically shut off. A pair of spaced apart wires are imbedded in an insulating tape with liquid cell sensor elements formed at spaced intervals about uninsulated sections of the wires. The tape is placed about the pipe to be monitored so as to collect the leaking water within the liquid cell sensor elements to electrically connect the conductors within a cell. Electronic circuitry actuates a servo to turn off a supply valve and/or sound an alarm. The water collecting elements eliminate unintended alarms due to condensation.

A prior art leak detection and shut-off apparatus for preventing damage from leaking hot water tanks shown in U.S. Pat. No. 5,334,973 features a unique three-layered sensor that completes encases the hot water tank thus detecting the occurrence of leaks anywhere on the tank. Circuitry controls the sensor that provides for accurate detection of even small amounts of moisture so that any potential leak problems can be remedied before a major spill occurs. The device also features a water shut off control mechanism plus audible alarm in the event a leak is detected. The unit is powered by connecting it to 110 house current. A 9 volt battery back-up is provided in case of power failures.

Another prior art device shown in U.S. Pat. No. 5,150,603 is a hydrocarbon vapor sensor which is simple and inexpensive and can easily detect the existence of hydrocarbon vapor. The device is temperature compensated so that a change in resistance due to a change in temperature is avoided and an accurate response is always provided. The sensor can be used in a system in which a number of sensors are provided at various depths to determine whether a leak or a ground spill has occurred.

A battery-powered, liquid-detection alarm and shut-off system including an elongated sensor, an electronic controller, and a spring biased shut-off valve assembly is shown in U.S. Pat. No. 5,008,650. The sensor comprises two partially exposed conductors separated by protruding ridges of insulation. The protruding-ridge configuration enables the sensor to detect small quantities of surface water and yet be insensitive to humidity. The electronic controller maximizes battery life and protects against false alarms caused by electrical interference. The shut-off valve assembly comprises a ¼-turn ball valve and a valve-actuating assembly. The valve is set by being manually cocked to an open position, engaging a lever actuated cam and preloading a valve shut-off spring. The valve is then closed by momentarily passing an electrical current through a temperature-activated memory-shaped spring located on the valve assembly. The current is supplied by the electronic controller in response to detection of liquid by the sensor. The heating of the spring from the induced current causes the tension of the memory-shaped spring to increase, releasing the lever actuated cam and permitting the preloaded valve shut-off spring to close the valve.

U.S. Pat. No. 4,843,327 describes a detection and location system, e.g. for liquid leaks, comprising a trunk line sensor cable and at least one branch line cable; each of the cables comprise two insulated conductors and two non-insulated conductors which are not connected to each other in the absence of a leak but which become connected upon occurrence of a leak. In the trunk line cable, the insulated conductors form part of a circuit which enables the location of a leak to be detected. In the branch line, one of the insulated conductors and one of the non-insulated conductors are connected so as to form a loop connecting the ends of the non-insulated conductors of the branch cable.

As shown in U.S. Pat. No. 4,710,353, a detector for detecting leaks of a corrosive liquid such as strong acids or bases is provided comprising a light guide core having a covering which generates heat upon contact with the liquid to be detected. The heat changes the light transmissivity of the light guide, which change can be measured. The covering comprises a porous polymer having a salt within its pores, such as an ammonium salt, which dissolves in the liquid to be detected and generates heat.

In U.S. Pat. No. 4,677,371, coaxial cable and a bare wire are aligned in parallel relationship and affixed within insulation covers which have openings therein so as to partly expose both the bare wire and the outer conductor of the coaxial cable to the atmosphere, thereby forming a leak-detecting sensor. By the use of resistance meters, the resistance of the core wire of the coaxial cable is monitored and utilized to detect both the presence and the location of a leak.

As disclosed in U.S. Pat. No. 4,386,269, to detect leaks from pipelines carrying fluids, especially oil, light is transmitted through a fibre-optic held in proximity with the pipeline. The fibre-optic is surrounded by a medium of which the refractive index is altered by the influence of the leaked fluid. In a preferred embodiment the medium is a silicone rubber of which the refractive index is normally lower than that of a quartz fibre optic, but of which the index increases to that of the quartz or above when oil soaks into it through a permeable cladding and an elastomeric protective layer, thus rendering the fibre optic non-internallyreflective so that light is absorbed. Control means linked to a light receiver detect that change and the position of the leak is located to within the length of the optic. In another embodiment, the medium is a liquid which is expelled from around the optic by the action of leaked fluid.

In another embodiment of the prior art, a first light beam generated from an electrical emitter (LED) is directed through a translucent material to a 45° wall in said translucent material, such that the light is reflected through the translucent material to a second 45° wall, which is at a 90° angle to the first wall, so that the light is again reflected back in the direction from which it came, and can be detected by a light sensing element near the emitter. If a substance, such as a liquid, comes in contact with the first and the second walls, the light is substantially refracted into the substance, and the intensity of the reflected light is greatly reduced; assuming the liquid is itself translucent. The reduction in the intensity of the reflected light is then indicative of the presence of the substance or liquid. This is then indicative of a leak condition.

In still another embodiment of the prior art, capacitance of a substance between parallel conductors is measured. Since the substances are presumed to have a dielectric constant different from the air normally between the parallel conductors, a difference in capacitance indicates the presence of the substance being monitored.

Several limitations of the prior art are known:

With electro-optical detectors, the reflective walls forming the 45° light reflecting angles must be kept very clean and the material must be translucent, with a high refractive index to the substance to be detected, to allow the refraction of light in an amount that will permit detection of the substance being monitored. This implies that considerable maintenance must be performed to keep the detector clean and in good working order, especially in a corrosive or nonresidue-depositing fluid environment. Moreover, the materials used typically have relatively poor resistance to corrosion from many of the chemicals that are monitored. The materials that must be used generally limit the maximum temperature within which they may be used (no more than 80° Centigrade) to avoid losing clarity and integrity of the shape. Further, such embodiments cannot detect very small amounts of leakage, are not very accurate, and are orientation sensitive. Another disadvantage is that normally the light emitter must be located within the sensing element, thereby requiring that potentially unsafe levels of electric power be delivered in chemically hazardous or explosion-prone environments.

Similar problems are encountered with implementations of fiber-optic devices for detecting liquid spills. The fiber-optic devices are affected by the reflectivity of the substance, lack of resistance to chemical interaction with the emitter and sensor, plugging of the device cavities, and lack of sensitivity. Furthermore, in many applications the light beam cannot be directed horizontally across the substance being monitored because of problems with parasitic reflections from, for example, the spill sump.

Capacitance sensors also suffer from problems with parasitics; in this case parasitic capacitances from, for example, the wall of a container. The capacitive sensor relies at least in part on actuation by the mass or density of the materials, which limits its sensitivity to the extent that it is not suitable for the detection of small amounts of leakage. Also, the capacitance which indicates the presence of a substance being monitored must be measured at high power levels for reliable results. High power levels are intrinsically unsafe in some environments. Further, fringing effects of the electric fields increase the likelihood of parasitic capacitances from other materials having an adverse effect or even causing a false actuation, and of interference with sensitive electronic equipment that may be nearby.

Previous detectors utilizing the resistive characteristics of the substance being measured have typically operated at high power levels, or have created possibly dangerous or deleterious conditions due to heating of the substance being monitored, the potential of a spark being generated, or a substantial and unsafe amount of leakage. Such devices have thus largely been confined to the detection of water or other inert materials. Further, the prior art does not teach the detection of very thin layers; such as 0.001 inches or better, which can be measured by this invention. In fact, the prior art teaches the detection of 0.25 inch or more layers; which is thought to be the lower limit for prior art methods.

SUMMARY OF THE INVENTION

Objects of the Invention:

An object of the present invention is to provide an improved more sensitive and broader range apparatus for detecting leakage of hazardous, including volatile or corrosive substances.

A further object of the present invention is to provide intrinsically safe means for detecting leaks or spills using very low (e.g., less than one microwatt) power levels with no sparking.

Still another object of the present invention to provide leak detector apparatus capable of detecting extremely small amounts of fluids and capable of being operated using either AC or DC power.

Also, an object of the present invention is to provide apparatus useful for detecting critical liquid levels with high precision and repeatability.

Another object of the present invention is to provide a detection system which operates reliably in extremes of pressure, corrosive fluids, and high temperatures.

It is also an object of the present invention to provide an apparatus of the type described that is securely mountable in different orientations easily and reliably.

A different object of the present invention is to provide an improved leak detection apparatus that can indicate the type of material is leaking.

Yet another object of the present invention is to provide leak detection apparatus using both the resistive or ionization characteristics and the capacitive characteristics of the substance being monitored to determine the type of material detected, such apparatus including signal-processing and -indicating circuits connected to a pair of accurately spaced and separated probes.

It is also an object of this invention to provide an apparatus for detecting spills and leaks, as well as for other purposes as will be shown below, that does not require resetting or human intervention when the condition detected is removed or corrected.

Another object of the invention is to provide apparatus which, when appropriately mounted, provides indication and warning of the absence of an acceptable level of fluid.

It is a further object of this invention to provide an apparatus for the detection of leaks, spills, or other conditions, using a probe which is insensitive to variable pressures, withstands high operating temperatures (as high as 230° Centigrade), and has excellent chemical resistance when made with materials such as gold, platinum, and Teflon.

Still another object of the invention is to provide an apparatus for the detection of leaks, spills, and other conditions, having a sensor that can be mounted at a relatively remote location which may have a hostile or dangerous environment or be at very high temperatures, while the results are monitored in an environment that is safe and benign.

It is an object of the present invention to provide an apparatus with both the level and quality of a fluid that can be monitored. An example is deionized water for semiconductor or other manufacturing, in which the water must be maintained above a certain resistance level, such as 28 megohms, with a warning being sounded if a predetermined level is not maintained.

A further object of the invention is to provide apparatus having a selectable threshold point at which the resistance of a fluid being detected causes a warning to be generated, such threshold being used to identify the fluid being detected.

It is a further object of the invention to provide apparatus including one or a multiplicity of remote probes, which might be in a hazardous, pressurized, corrosive, or high-temperature environment, and be connected to a single warning or control module, for independently detecting fluids of possibly different composition and nature.

BRIEF SUMMARY OF THE INVENTION

The present invention includes a detector having two or more pins, preferably clad with a non-corrosive material such as gold or platinum, and mounted in a carefully spaced relationship with each other in a chemically inert housing, and electronic circuitry for measuring the resistance or conductively due to ionization through a substance such as a liquid or vapor which comes in contact with the probes. The apparatus measures the resistance at a very low direct current power level, such as less than one microwatt, in order that hazardous materials are not made more hazardous. Alternatively, the detector may be operated at a very low alternating current power level, such as less than one microwatt, to detect both the resistance and capacitance through the substance so that the characteristic relation of the resistance to the capacitance can be determined and thereby provide a qualitative analysis of the substance. A detector in accordance with the present invention is useful for detecting leaks and fluid levels, and can be used to identify particular types of fluids.

ADVANTAGES OF THE INVENTION

This invention permits the detection of leakage of substances, such as hazardous liquids or vapors, at low power levels, and low voltages, without making the presence of the hazardous substances more hazardous as a result of induced heating.

A further advantage of the present invention is that the sensitivity of the apparatus allows very thin, such as 0.001 inch layers of fluids, or electrolyte-saturated atmospheres, to be detected.

These and other objects and advantages of the present invention will become apparent to those skilled in the art following a reading of the detailed description and of the preferred embodiment as depicted in the several figures of the drawing.

IN THE DRAWING

FIG. 4 is a schematic diagram illustrating the principal electrical components of the preferred embodiment;

FIG. 5 is a schematic diagram illustrating the use of alternating current with the invention to determine the ratio of the capacitive and the resistive impedance of a substance;

DETAILED DESCRIPTION OF THE PREFERRED EMBODIMENTS

Figure 1:
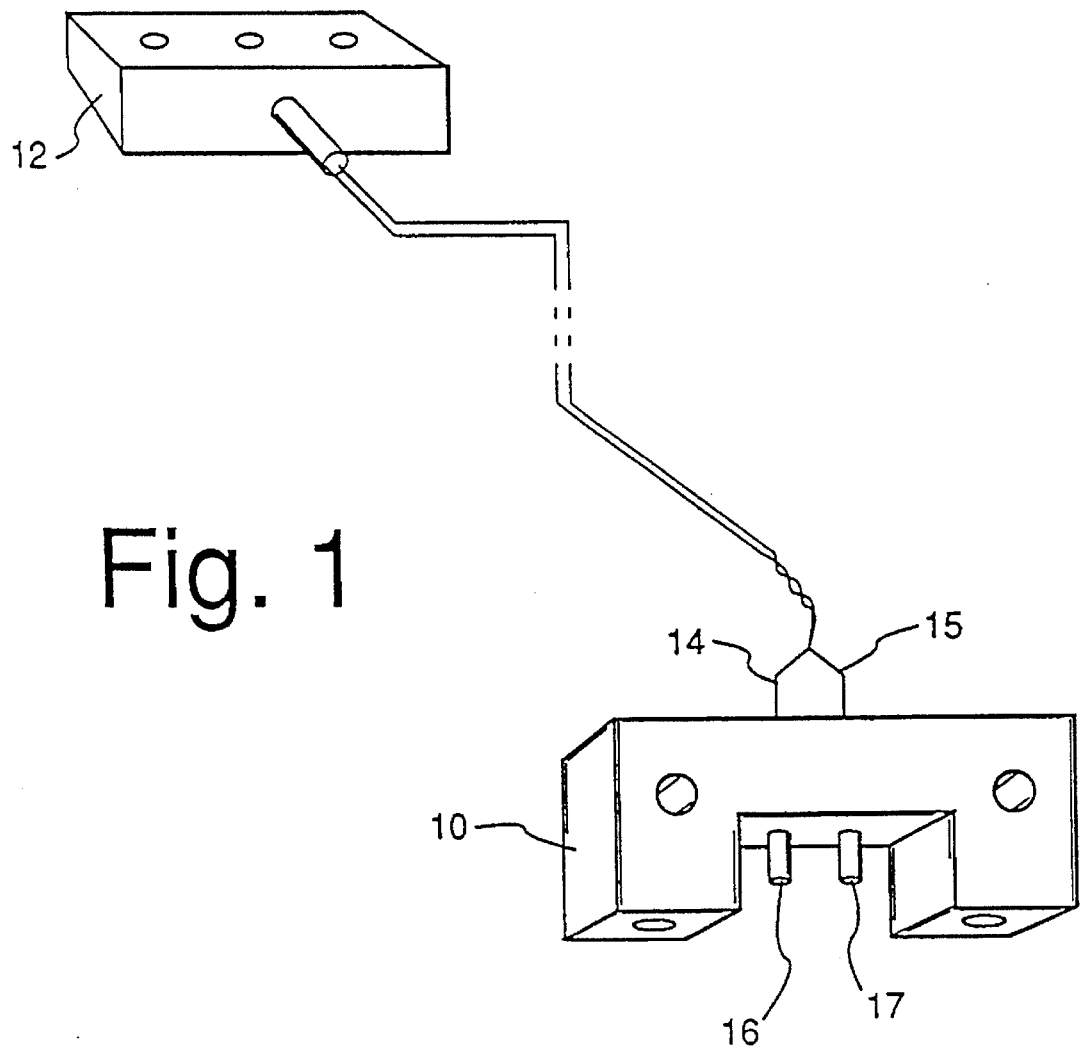
FIG. 1 shows a detector system or probe in accordance with a preferred embodiment of the present invention.

Referring now to FIG. 1 of the drawing, a detector system in accordance with the present invention is generally shown to include a sensing probe 10 and an electronic control and indicating module 12 electrically connected together by a twisted pair of conductors 14 and 15. The module 12 may be internally battery-powered or as depicted in detail below externally powered.

Figure 2:
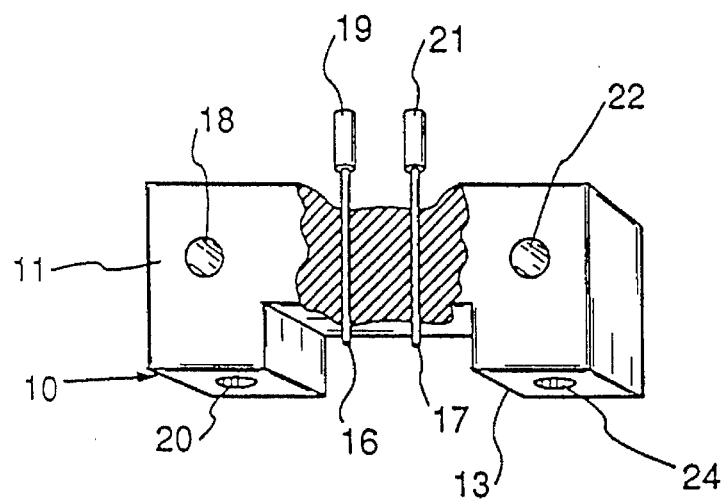
FIG. 2 is a partially broken perspective illustration showing a probe head in accordance with a preferred embodiment of the present invention.

As is more clearly shown in FIG. 2, the sensing probe 10 includes a block 11 of electrically insulative and chemically inert material such as Teflon having a pair of conductive electrodes in the form of pins 16 and 17 disposed so that they extend through the block and into a recess 13 formed in the bottom of block 11. Pins 16 and 17 have a precise spacing between them for reasons that will become apparent, and are constructed of a chemically inert material such a gold or platinum. Male or female connectors 19 and 21 may be affixed to the upper ends of pins 16 and 17 to facilitate connection to the twisted pair 14, 15. Probe 10 has mounting holes 18, 20, 22, and 24 disposed to accommodate either a preferred horizontal orientation of the pins 16 and 17 or an alternative orientation.

Figure 3:
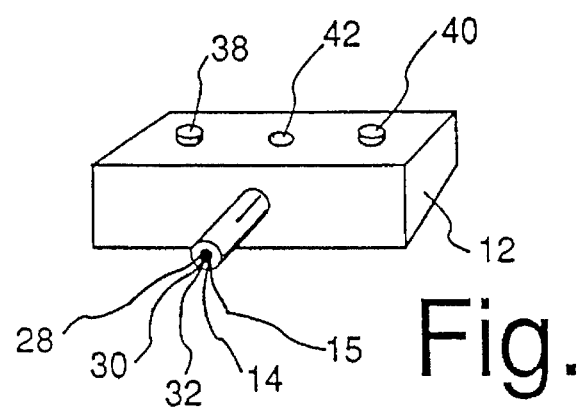
FIG. 3 is a perspective view illustrating the remotely located housing wherein the electrical elements of the preferred embodiment are housed.

The electronic control module 12 is depicted in FIG. 3 as having five wires connecting to it, including in addition to the probe leads 14 and 15, a power wire 28, a ground wire 30, and an output signal wire 32. The module 12 has a protruding green LED 38 and a protruding red LED 40 respectively forming visual no-leak and leak status indicators. The module 12 also has a mounting hole 42 extending through it to receive a 8 mounting screw for appropriately mounting the device, so that it may be disposed to make the green and red LEDs 38 and 40 easily visible.

FIG. 4 of the drawing is a schematic of the electronic circuit disposed within the control module. The circuit has five external connections 114, 116, 118, 120, and 122. An external connector pin 114, to which power wire 28 will be connected, is connected to a first end 44 of a fuse 46. The opposite end of fuse 46 is connected to one side of a capacitor 48 and to an input 50 of a voltage regulator 52. The output 51 of voltage regulator 52 is connected to capacitors 56 and 60, as well as a terminal 62 marked VCC. Voltage regulator and capacitors 56 and 60 maintain terminal 62 at +5 volts. Pin 116 is a ground connection as indicated at 54. Note that all terminals marked VCC are connected to terminal 62 as indicated by the dashed lines 63. External connection 116 is connected to ground via ground wire 30 (FIG. 3) in the system of which this schematic is a part. The method of implied connection in which a point is associated with a ground symbol 54, a technique well known in the art, is used to show a ground connection without the connection being explicitly shown. This technique for implying a ground is used throughout the schematic. All ground symbols 54 are connected to ground, and VCC symbols have an implied connection to terminal 62 and via lead 58 to the output pin 51 of the voltage regulator 52. Consequently, nodes that connect only to ground or to VCC are not numbered in the schematic.

External connection 118 is connected via a lead 64 to one end of a fuse 66 with a value of 60 mA, the other end of which is connected to resistors 76 and 78 via a node 73. The opposite end of resistor 78 is connected to ground. The upper end of resistor 76 is connected via node 74 to the anode end of a diode 70 and to one end of resistor 68. The other end of resistor 68 is connected to VCC. Node 73 is connected to the negative input pin 2 of voltage comparator 86 having its positive input 3 connected to the junction 80 of two resistors 82 and 84 connected in series between VCC and ground. Pin 7 of voltage comparator 86 is connected to VCC and pin 4 is connected to ground. The voltage comparator output pin 6 is connected via a lead 94 to a circuit node 95. Pin 8 of voltage comparator 86 is connected to one side of a compensating capacitor 92. The opposite side of 92 is connected to ground.

A feedback resistor 88 is connected between voltage comparator output pin 6 and input 3. A resistor 84 connects node 95 to the base 102 of an NPN transistor 104, the emitter of which is connected to ground. The collector of transistor 104 is connected to a node 106, which is connected via a resistor 108 to VCC and to the anode of the LED 38. The cathode of diode 38 is connected to ground.

A resistor 100 is connected between node 95 and the base of an NPN transistor 110, the emitter of which is connected to ground. The collector 112 of transistor 110 is connected to external connection 122 which is connected to the output wire 32 (FIG. 3). Node 95 is also connected by a resistor 98 to the anode of the LED 40. The cathode of diode 40 is connected to ground.

In operation, a voltage with positive values between 8 VDC and 28 VDC is connected to external connection 114. Zero VDC, or ground, is connected to external connection 116 which is internally connected to pin 120 in this implementation, and thus to all other ground points in the schematic. The operation of the subcircuit containing voltage regulator 52 is such that all points marked VCC in the schematic are maintained at a precise positive value of +5 VDC. The purpose of capacitors 48, 56, and 60 is to suppress or reduce the effects of undesirable transient voltages, commonly known as noise. VCC is impressed on resistor 68, which has a value of 5100 ohms and causes a current to flow into the anode of diode 70. This causes a voltage of 0.6 VDC, more or less, to be established at 74. Because resistor 76, which has a value of 20 megohms, and resistor 78, which also has a value of 20 megohms, are of the same value, and assuming a detector dry condition in which no significant current flows from external connection 118 to external connector 120 through the sensor unit (FIG. 1) that will be connected between them, the probe voltage at node 73 and thereby on pin 2 of 86 will be 0.3 VDC, approximately.

The values of resistor 84 (1 megohm) and resistor 82 (39 K ohms) are such that the voltage on node 80 is 0.2 VDC, approximately. The influence of resistor 88 is too small to materially affect the value of the voltage at node 80 when the probe senses a dry condition, because at that time the output of the voltage comparator 86 is at approximately zero VDC, though it may be at a slightly higher voltage, such as 0.2 VDC. This condition obtains because 0.3 VDC on pin 2 of voltage comparator 86 and 0.2 VDC on pin 3 indicates that the voltage on pin 2 will be higher or more positive than the voltage on pin 3, and the specifications are such that the output pin 6 of voltage comparator 86 is forced to a relatively negative or, in this schematic, nearly zero voltage. The low or zero voltage at node 95 causes a low or zero voltage to appear on the bases of NPN transistors 104 and 110, as well as the anode of LED 40 so all three of these devices are in the off or non-conducting condition.

This means that LED 40 will not be lighted. By the same reasoning, the current flowing through resistor 108 cannot flow through NPN transistor 108, which is off, and will therefore flow through LED 38, which will emit a green light. Also, NPN transistor 110 is off, as mentioned, so no current flows into it from external connection 122 and any external device connected to 122 (and thereby to lead 15 of FIG. 3) will not have a power circuit enabled through it, so it will also be off.

When a wet condition is detected as a result of the fluid-coupling of probe pins 16 and 17 together, the resistance, or conductance due to ionization, of the fluid between connection 118 (and lead 14 of FIG. 3), and connection 120 (lead 15 of FIG. 3) will decrease, with the current that flows through it causing node 73 and thereby pin 2 of voltage comparator 86 to be reduced in voltage below the voltage on pin 3. This will cause pin 6 of the voltage comparator 86 to begin to go to a more positive voltage. As a consequence, a current will begin to flow through resistor 88 into resistor 82, which will cause the voltage on pin 3 of voltage comparator 86 to become more positive, increasing the difference in the voltage on pin 3 over pin 2, and causing pin 6 to rapidly become more positive. This is called "hysteresis" in the art.

The positive voltage on pin 6 of voltage comparator 86 causes a positive voltage at node 95, which in turn causes a positive voltage (or current) to be applied to the bases of NPN transistors 104, 110 and the anode of LED 40. All three devices are turned on thereby, and LED 40 emits a red light. Meanwhile, NPN transistor 104 causes the current flowing in resistor 108 to flow around LED 38. LED 38 is thus turned off and ceases to emit any light. At the same time, NPN transistor 110 is also turned on, and allows a current to flow into its collector through external connection 122 which causes an external device connected to 122 to be powered or turned on, causing, for example, an alarm to sound, or an external machine to be turned off (or on).

The hysteresis of voltage comparator 86 mentioned above is set such that when the wet condition at probe 10 is removed, and a dry condition is established, the output of voltage comparator 86 on pin 6 returns to a low or zero voltage automatically; therefore the module is said to have automatic reset.

Reiterating the operation of the electronic control module, in the absence of a probe wetting fluid substance the green LED will be energized. Upon the detection of a substance, the green LED will be turned off (become unlighted) and the red LED will be turned on, indicating the presence of the fluid substance. At the same time, the output lead 32 will be connected to ground through a low resistance path, and is therefore available to power a relay, buzzer, or other warning device for audibly or visually indicating the presence of the substance, or for turning off machinery as desired.

Referring to FIG. 5 of the drawing, in an alternative implementation, a variable-frequency alternating power source 124, which preferably has a large source impedance, is applied to external connection 118. Provided that the source impedance is of an appropriate value and that the frequency is properly adjusted to the spacing of the sensor pins 16 and 17 and the characteristics of the substance "S" being detected, the resonant frequency of the parallel combination of the resistive impedance 126 and capacitive reactance 128 of the substance S being monitored can be determined. The maximum impedance of a resistor-capacitor combination will be found at the resonant frequency of the combination, which is approximately equal to the frequency at which the resistive impedance equals the capacitive reactance. So by adjusting the frequency of source 124 until the amplitude of the alternating current or voltage developed across this impedance is large enough to cause voltage comparator 86 to drive its pin 6 to a high voltage, the ratio of the resistive and capacitive can be determined. So long as the frequency is maintained at or near resonance, the same circuit for resistive sensing described above could also be used for determining the resonant frequency with the same red and green indications and the same output drive, together with automatic reset as before. Some modification of the circuit may be desirable but is not believed to be necessary. Since substances, such as barium titanate, which is an insulator but has a very high dielectric constant, have a ratio of resistance to dielectric constant that is not exactly related; this allows the determination of the types of substances in a way that is not possible with light sensing, capacitive sensing, or resistive sensing only. Also, since the resonant frequency will be unique for many substances, this will allow for quantifying mixtures of some substances. For example, if a first substance, such as ionized water was known to be resonant at a first frequency, and a second substance such as a corrosive chemical, was known to be resonant at a second frequency, a third resonant frequency half way between the first resonant frequency and the second resonant frequency would indicate equal parts of the ionized water and the corrosive chemical existed in the substance being monitored.

Note that, using the principles by which so-called shunt resonant oscillators are designed, such as in the oscillators commonly used in "quartz" watches and clocks, a circuit could be realized that would automatically seek the resonant frequency of a substance or of a mixture of substances. The circuitry to support this form of usage is not shown explicitly herein but in light of the above discussion could easily be implemented by one skilled in the art.

Figure 6:
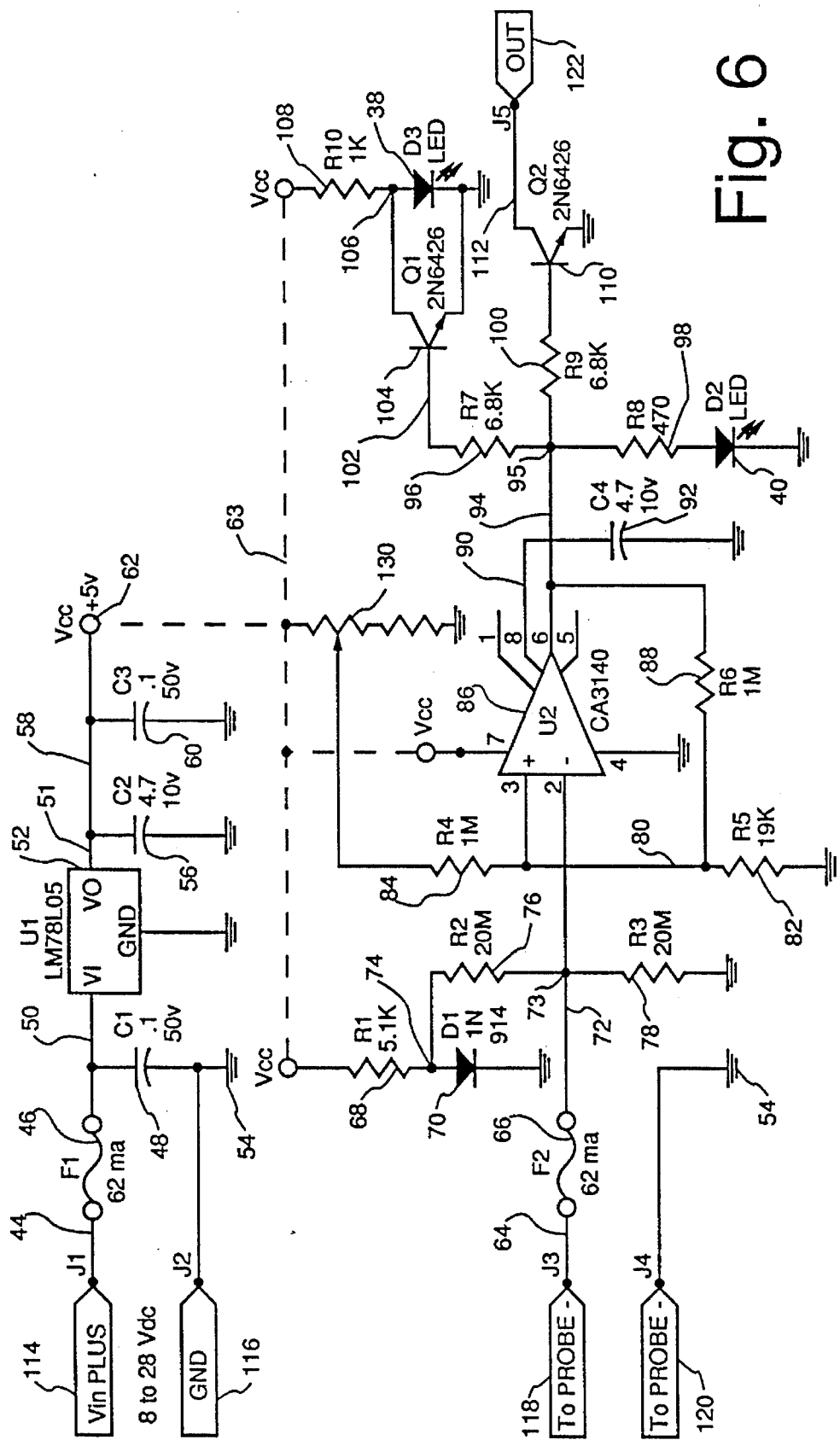
FIG. 6 is a schematic diagram illustrating the use of a variable resistance to allow adjustment of the point at which the detector will be respond to a substance.

In FIG. 6 another alternative embodiment of the sensing and control circuit of the present invention is depicted and is substantially the same as that depicted in FIG. 4, except that the top side of resistor 84 is connected to VCC through a potentiometer 130 which allows the value of the reference voltage of voltage comparator 86 to be adjusted. Since the distance separating the sensing pins is constant, this permits the triggering potential of the voltage comparator to be selected so as to predetermine the type or types of fluid substances that will be sensed by the system.

Figure 7:
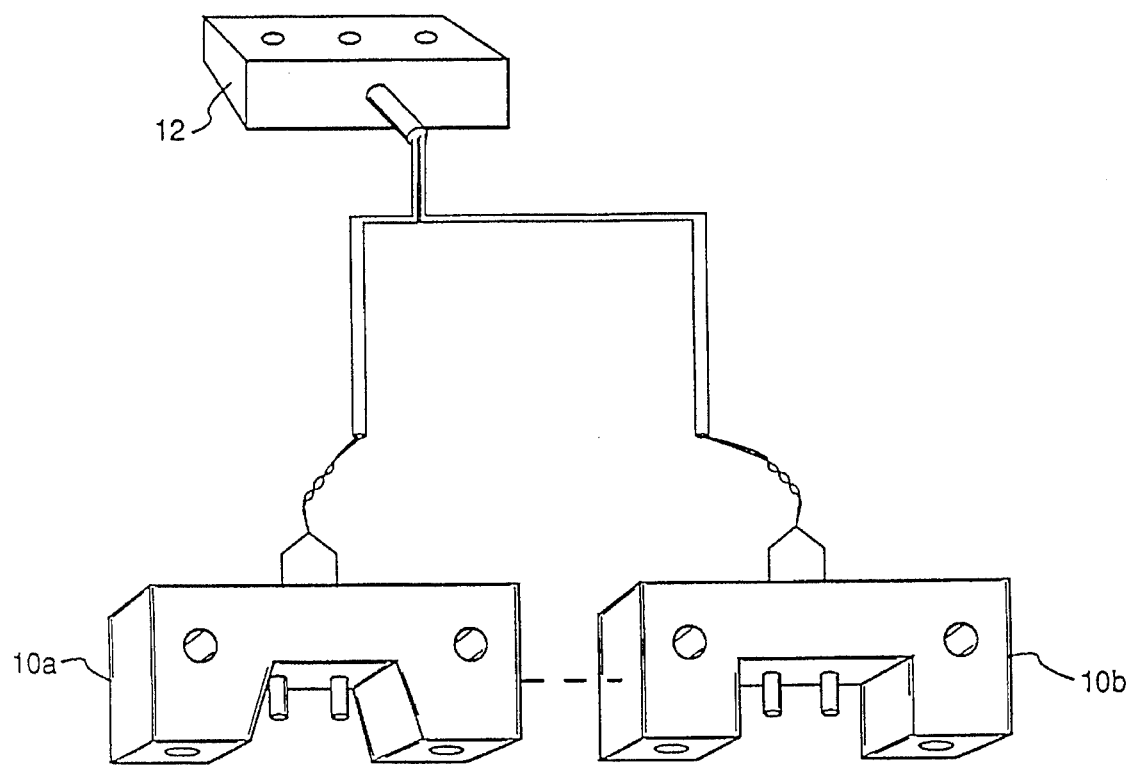
FIG. 7 is an embodiment of a system including multiple detectors or remotely located sensing probes with a single electronic control module.

FIG. 7 depicts a plurality of sensing probes 10a, 10b, . . . , connected in parallel to the module 12. The probes may be of identical configurations and positioned at remote locations relative to each other, or may be located to monitor different volumes of space. Alternatively, the spacing between the respective electrodes of the several probes may be varied so as to make each probe sensitive to a different type of fluid.

A possible extension of the present invention may include a means for repetitively sweeping the frequency of the source 124 over a selected range of frequencies in order to detect resonance at a frequency indicative of the fact that one or more particular types of fluids have come into contact with the electrodes 16 and 17.

Although the present invention has been described above in terms of a specific embodiment, it is anticipated that alterations and modifications thereof will no doubt become apparent to those skilled in the art. It is therefore intended that the following claims be interpreted as covering all such alterations and modifications as fall within the true spirit and scope of the invention.

I claim:

1. A detector system using extremely low power to sense the presence or absence of an inert or hazardous fluid comprising:

a sensing probe having a pair of electrically conductive, non-corrosive sensing electrodes disposed in a predetermined spaced relationship; and an electronic control module electrically connected to said probe for applying a probe energizing potential to one of said sensing electrodes and for connecting the other sensing electrode to a circuit ground, including power supply means for developing a regulated predetermined supply voltage of less than 10 volts, voltage and current-limiting means for receiving the supply voltage and for developing a probe voltage that is at least an order of magnitude lower than said supply voltage, and for applying said probe voltage to said one sensing electrode, said voltage and current-limiting means limiting the power applied to said sensing electrodes to approximately 1 microwatt or less, indicator means for indicating current flow or the lack thereof between said sensing electrodes, and comparator means for comparing the voltage drop developed across said sensing electrodes to a reference voltage and for causing said indicator means to have one indicating state when a particular type of fluid is in contact with said sensing electrodes, and for having another indicating state when said particular type of fluid is not in contact with said sensing electrodes.

2. A low power detector system as recited in claim 1, wherein said sensing electrodes are clad in a non-corrosive metal and are mounted in a block of non-corrosive, non-conductive material.

3. A low power detector system as recited in claim 2, wherein said sensing electrodes are formed by elongated pins disposed parallel to each other and extending through said block.

4. A low power detector system as recited in claim 3, wherein said indicator means includes at least a first light-emitting diode and means responsive to the output of said comparator means for energizing said first light-emitting diode when said particular type of fluid is not in contact with said sensing electrodes, and for causing said first light-emitting diode to be de-energized when said particular type of fluid is in contact with said electrodes.

5. A low power detector system as recited in claim 4, wherein said indicator means further includes a second light-emitting diode responsive to an output generated by said comparator means and operative to develop a visual indication when said particular type of fluid is in contact with said electrodes.

6. A low power detector system as recited in claim 5, wherein said electronic control module further includes an output terminal to which a controllable external device may be operatively connected, and a switching means responsive to an output generated by said comparator means and operative to control said external device.

7. A low power detector system as recited in claim 1, wherein said power supply means develops a supply voltage of approximately five volts and said voltage and current-limiting means develops an energizing potential of less than one volt for application to said one electrode.

8. A low power detector system as recited in claim 1, wherein said indicator means includes at least a first light-emitting diode and means responsive to the output of said comparator means for energizing said first light-emitting diode when said particular type of fluid is not in contact with said sensing electrodes, and for causing said first light-emitting diode to be de-energized when said particular type of fluid is in contact with said electrodes.

9. A low power detector system as recited in claim 8, wherein said indicator means further includes a second light-emitting diode responsive to an output generated by said comparator means and operative to develop a visual indication when said particular type of fluid is in contact with said electrodes.

10. A low power detector system as recited in claim 9, wherein said electronic control module further includes an output terminal to which a controllable external device may be operatively connected, and a switching means responsive to an output generated by said comparator means and operative to control said external device.

11. A low power detector system as recited in claim 1, and further comprising a variable frequency-alternating voltage source for applying alternating electrical energy of a selected frequency or range of frequencies across said electrodes and in addition to said probe voltage whereby the presence of a particular type of fluid in contact with said electrodes may be selectively detected as a result of a resonance condition occurring in the electrical energy applied across said electrodes.

12. A low power detector system as recited in claim 11, wherein said indicator means includes at least a first light-emitting diode and means responsive to the output of said comparator means for energizing said first light-emitting diode when said particular type of fluid is not in contact with said sensing electrodes, and for causing said first light-emitting diode to be de-energized when said particular type of fluid is in contact with said electrodes.

13. A low power detector system as recited in claim 12, wherein said indicator means further includes a second light-emitting diode responsive to an output generated by said comparator means and operative to develop a visual indication when said particular type of fluid is in contact with said electrodes.

14. A low power detector system as recited in claim 13, wherein said electronic control module further includes an output terminal to which a controllable external device may be operatively connected, and a switching means responsive to an output generated by said comparator means and operative to control said external device.

15. A low power detector system as recited in claim 1, wherein said power supply means develops a supply voltage of approximately five volts and said voltage and current-limiting means limits current flow from said one electrode to the other to one micro amp or less.

16. A low power detector system as recited in claim 1, wherein said power supply means develops a supply voltage of approximately five volts and said voltage and current-limiting means limits the power applied across said electrodes to one microwatt or less.

17. Detector apparatus using extremely low power to detect the leakage of an inert or hazardous fluid into a particular volume of space, comprising:

a sensing probe having a pair of sensing electrodes adapted to extend into said volume of space;

power supply means for applying a voltage across said electrodes;

electronic means for detecting current flowing between said electrodes as a result of fluid leaking into said volume of space and electrically coupling said electrodes, and for developing a responsive output signal, said electronic means including voltage and current-limiting means for causing the voltage applied across said electrodes to be substantially less than one volt and the power applied to said electrodes to be less than one microwatt, and comparator means for comparing the voltage developed across said electrodes to a reference voltage and for causing said output signal to have a first value in the absence of leakage into said volume of space and to have a second value in the presence of leakage into said volume of space; and indicator means responsive to said output signal for providing an indication of the leak.

18. Detector apparatus as recited in claim 7, wherein said sensing electrodes are clad in a non-corrosive metal and are mounted in a block of non-corrosive, non-conductive material.

19. Detector apparatus as recited in claim 18, wherein said sensing electrodes are formed by elongated pins disposed parallel to each other and extending through said block.

20. Detector apparatus as recited in claim 19, wherein the voltage applied across said electrodes is less than one volt.

21. Detector apparatus as recited in claim 20, wherein said indicator means includes at least a first light-emitting diode and means responsive to the output of said comparator means for energizing said first light-emitting diode when said particular type of fluid is not in contact with said sensing electrodes, and for causing said first light-emitting diode to be de-energized when said particular type of fluid is in contact with said electrodes.

22. Detector apparatus as recited in claim 21, wherein said indicator means further includes a second light-emitting diode responsive to an output generated by said comparator means and operative to develop a visual indication when said particular type of fluid is in contact with said electrodes.

23. Detector apparatus as recited in claim 22, wherein said electronic control module further includes an output terminal to which a controllable external device may be operatively connected, and a switching means responsive to an output generated by said comparator means and operative to control said external device.

24. Detector apparatus as recited in claim 23, and further comprising a variable frequency-alternating voltage source for applying alternating electrical energy of a selected frequency or range of frequencies across said electrodes and in addition to said probe voltage, whereby the presence of a particular type of fluid in contact with said electrodes may be selectively detected as a result of a resonance condition occurring in the electrical energy applied across said electrodes.

25. Detector apparatus as recited in claim 17, wherein said sensing probe is adapted to be mounted at a selected level above the bottom of a container so as to provide an extremely accurate and repeatable fluid level sensing device.

26. Detector apparatus as recited in claim 17, wherein by tuning said electronic means to respond to a particular resistance or conductance due to ionization, an alarm related to the quality of the monitored fluid substance may be generated.

* * * * *